(12) United States Patent
Patterson et al.

(10) Patent No.: US 8,686,355 B2
(45) Date of Patent: Apr. 1, 2014

(54) DETECTION SYSTEM ASSEMBLY, DRYER CARTRIDGE, AND REGENERATOR AND METHODS FOR MAKING AND USING THE SAME

(75) Inventors: Michael Edgar Patterson, Amesbury, MA (US); Matthew Edward Knapp, Marblehead, MA (US)

(73) Assignee: Morpho Detection, LLC, Newark, CA (US)

( * ) Notice: Subject to any disclaimer, the term of this patent is extended or adjusted under 35 U.S.C. 154(b) by 184 days.

(21) Appl. No.: 13/415,359

(22) Filed: Mar. 8, 2012

(65) Prior Publication Data
US 2013/0234013 A1    Sep. 12, 2013

(51) Int. Cl.
*H01J 49/00* (2006.01)
(52) U.S. Cl.
USPC .............................. 250/288; 250/282; 96/118
(58) Field of Classification Search
USPC ........................................................ 250/288
See application file for complete search history.

(56) References Cited

U.S. PATENT DOCUMENTS

| | | | |
|---|---|---|---|
| 5,405,781 A * | 4/1995 | Davies et al. | 436/52 |
| 5,491,337 A | 2/1996 | Jenkins et al. | |
| 5,622,544 A * | 4/1997 | Shamine et al. | 96/134 |
| 6,815,670 B2 | 11/2004 | Jenkins et al. | |
| 7,377,188 B2 * | 5/2008 | Jenkins | 73/863.23 |
| 7,942,033 B2 | 5/2011 | Jenkins | |

* cited by examiner

*Primary Examiner* — Phillip A Johnston
(74) *Attorney, Agent, or Firm* — Armstrong Teasdale LLP

(57) ABSTRACT

A detection system assembly is provided. The detection system assembly includes a detector system including a housing having a sample port configured to receive a sample of an unknown substance, a detector assembly in flow communication with the sample port, and a pump in flow communication with the detector assembly. The detection system assembly further includes a dryer cartridge removably coupled to an outer surface of the housing of the detector system. The dryer cartridge is in flow communication with the pump and the detector assembly.

21 Claims, 16 Drawing Sheets

DETECTION SYSTEM ASSEMBLY, DRYER CARTRIDGE, AND REGENERATOR AND METHODS FOR MAKING AND USING THE SAME

BACKGROUND OF THE INVENTION

The embodiments described herein relate generally to a detection system assembly, and more particularly, to a detection system assembly having a removable dryer cartridge and an external regenerator for drying the dryer cartridge.

At least some known detection systems generate an air flow to carry molecules from a sample material to a detector, e.g., an ion mobility spectrometer or an ion trap mobility spectrometer. More specifically, the sample and ambient air are heated to remove contaminates from the air and to cause molecules from the sample to flow with the air flow. The sample molecules can be analyzed to determine whether contraband is present. As used herein, the term "contraband" refers to illegal substances, explosives, narcotics, weapons, special nuclear materials, dirty bombs, nuclear threat materials, a threat object, and/or any other material that a person is not allowed to possess in a restricted area, such as a border crossing and/or an airport.

At least some known ion mobility spectrometer (IMS) and/or ion trap mobility spectrometer (ITMS) detection systems use a desiccant material, such as a molecular sieve, to maintain low humidity levels in a detection loop. When the sieve becomes saturated with moisture, maintenance is performed on the detection system to replace the "wet" sieve with a "dry" sieve material. Another known detection system includes at least one dryer in flow communication with the air flow. The dryer removes moisture from an air flow and the dry air flow facilitates carrying sample molecules to the detector. However, the dryer becomes wetted and must be periodically dried. With at least some known detection systems, in order to dry the dryer, the entire detection system is taken offline until the dryer is sufficiently dried.

Other known systems include a dual dryer system in which one dryer is used to dry air while the other dryer is regenerated. Such a detection system is not taken offline to dry the dryer and/or to replace a sieve.

The above-described detection systems generally are placed on a desktop. A sample is collected then taken to the detection system for analysis of the sample.

BRIEF DESCRIPTION OF THE INVENTION

In one aspect, a detection system assembly is provided. The detection system assembly includes a detector system including a housing having a sample port configured to receive a sample of an unknown substance, a detector assembly in flow communication with the sample port, and a pump in flow communication with the detector assembly. The detection system assembly further includes a dryer cartridge removably coupled to an outer surface of the housing of the detector system. The dryer cartridge is in flow communication with the pump and the detector assembly.

In another aspect, a dryer cartridge for use with a detector system is provided. The dryer cartridge includes an inlet configured to receive an air flow, an outlet configured to discharge air, a capture portion between the inlet and the outlet, and a coupling plate configured to removably couple the dryer cartridge to an outer surface of a housing of the detector system. The capture portion is configured to capture at least one of liquid particles and liquid vapors from the air flow through the inlet. The dryer cartridge is configured to receive the air flow from a first component of the detector system and discharge the air into at least a second component of the detector system when the dryer cartridge is coupled to the detector system.

In yet another aspect, a regenerator for use with a dryer cartridge is provided. The regenerator includes a housing and a heater. The housing includes a chamber configured to receive at least a portion of the dryer cartridge, and the heater is positioned within the housing. The heater is configured to heat the dryer cartridge when positioned in the chamber.

In still another aspect, a method for assembling a detection system assembly including a detector system and a dryer cartridge is provided. The method includes providing the detector system including a housing, providing the dryer cartridge, and removably coupling the dryer cartridge to an outer surface of the housing of the detector system to form the detection system assembly.

In one aspect, a method for assembling a dryer cartridge for use with a detector system is provided. The method includes providing a housing, a sieve, and a coupling plate, positioning the sieve adjacent the housing to form a capture portion of the dryer cartridge, and coupling the coupling plate to the housing to secure the sieve between the coupling plate and the housing.

In another aspect, a method for using a detection system assembly that includes a detector system and a dryer cartridge coupled to the detector system is provided. The method includes inserting a sample of a substance into a detector assembly of the detection system assembly, directing an air flow through the detector assembly to transport the substance through the detector assembly, including directing the air flow through the dryer cartridge to remove at least one of liquid particles and liquid vapors from the air flow, and identifying at least one of a chemical and a biological material of the substance using an output of the detector assembly.

In yet another aspect, a method for using a regenerator with a dryer cartridge is provided. The method includes providing the regenerator including a housing having a chamber and a heater positioned within the housing, positioning the dryer cartridge within the chamber, and performing a drying cycle by heating the dryer cartridge within the chamber using the heater.

In still another aspect, a method for operating a regenerator to dry a dryer cartridge is provided. The method includes performing a heating cycle during which the dryer cartridge is heated to a temperature within a predetermined range of temperatures, and performing a cooling cycle during which the dryer cartridge is cooled to a predetermined temperature that is below the predetermined range of temperatures. The heating cycle and the cooling cycle define a drying cycle.

BRIEF DESCRIPTION OF THE DRAWINGS

FIG. 1 is a perspective view of an exemplary detection system assembly.

FIG. 2 is a blown-up perspective view of the detection system assembly shown in FIG. 1 with a dryer cartridge removed from a detector system.

FIG. 3 is a schematic view of the detection system assembly shown in FIGS. 1 and 2.

FIG. 4 is a perspective view of an exemplary dryer cartridge that may be used with the detection system assembly shown in FIGS. 1-3.

FIG. 5 is an exploded front perspective view of the dryer cartridge shown in FIG. 4.

FIG. 6 is an exploded rear perspective view of the dryer cartridge shown in FIG. 4.

FIG. 7 is another exploded rear perspective view of the dryer cartridge shown in FIG. 4.

FIG. 8 is a rear view of an exemplary housing that may be used with the dryer cartridge shown in FIGS. 4-7.

FIG. 9 is a flowchart of an exemplary method for making the detection system assembly shown in FIGS. 1-8.

FIG. 10 is a flowchart of an exemplary method for operating the detection system assembly shown in FIGS. 1-8 in an Idle Mode.

FIG. 11 is a flowchart of an exemplary method for operating the detection system assembly shown in FIGS. 1-8 in a Sampling Mode.

FIG. 12 is a front perspective view of an exemplary regenerator that may be used with the dryer cartridge shown in FIGS. 1-8 with a cover in a closed position.

FIG. 13 is a front perspective view of the regenerator shown in FIG. 11 with the cover in an open position.

FIG. 14 is a schematic view of the regenerator shown in FIGS. 12 and 13.

FIG. 15 is a flowchart of an exemplary method for using the regenerator shown in FIGS. 12-14.

FIG. 16 is a flowchart of an exemplary method of operation of the regenerator shown in FIGS. 12-14.

DETAILED DESCRIPTION OF THE INVENTION

The embodiments described herein provide a drying device used to regenerate a dryer, or a sieve, used in an ion mobility spectrometer (IMS) or in an ion trap mobility spectrometer (ITMS). More specifically, the embodiments described herein provide a chemically-inert, high-temperature-compatible dryer cartridge that is integrated in the IMS/ITMS detection system assembly and that can be easily removed from the detection system assembly to be regenerated in an external drying apparatus. This external apparatus is embodied as a regenerator that accepts a "wet" dryer cartridge, heats the dryer cartridge, and provides an air flow through the dryer cartridge to purge out moisture and contaminates from the molecular sieve so the dryer cartridge can be re-used in the detection system assembly. In a particular embodiment, at least two drying cartridges are supplied with the detection system assembly to ensure that at least one cartridge is available while another dryer cartridge is being "regenerated" in the external dryer.

The regenerator described herein is automated to ensure proper temperature, air flow, heating times, and cooling times are achieved. By using the external regenerator and the re-useable high-temperature dryer cartridges, maintenance downtimes and/or consumable costs to the end customer are reduced as compared to the known detection systems described above.

Figure 1:
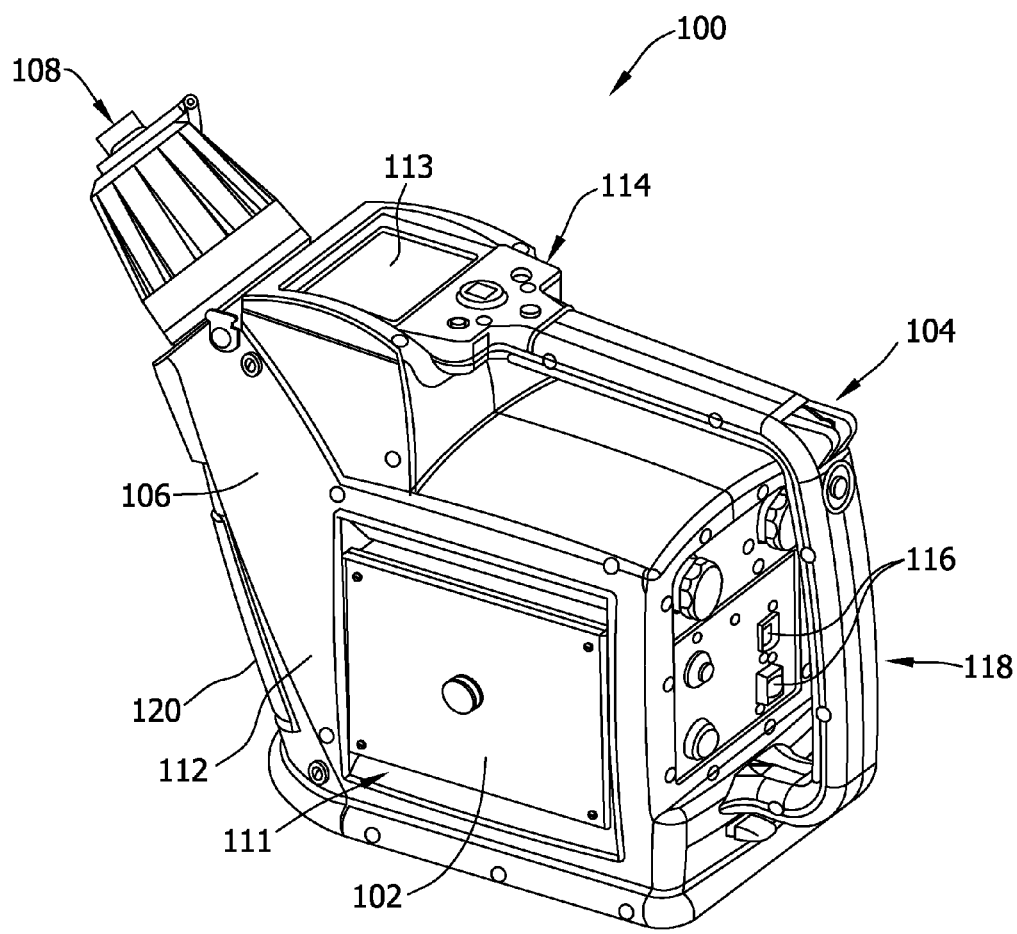
FIGS. 1-16 show exemplary embodiments of the systems and methods described herein.
Figure 2:
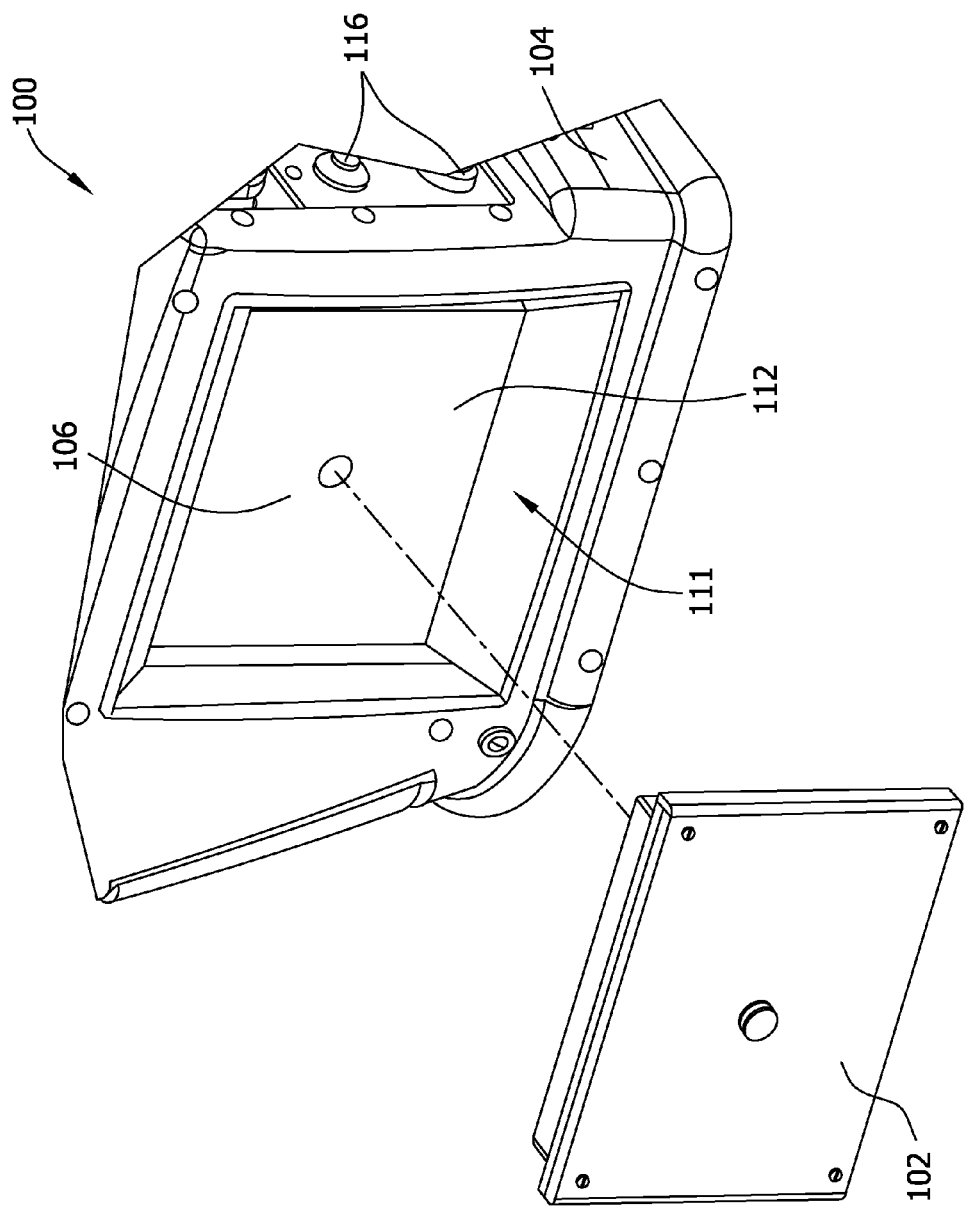
Figure 3:
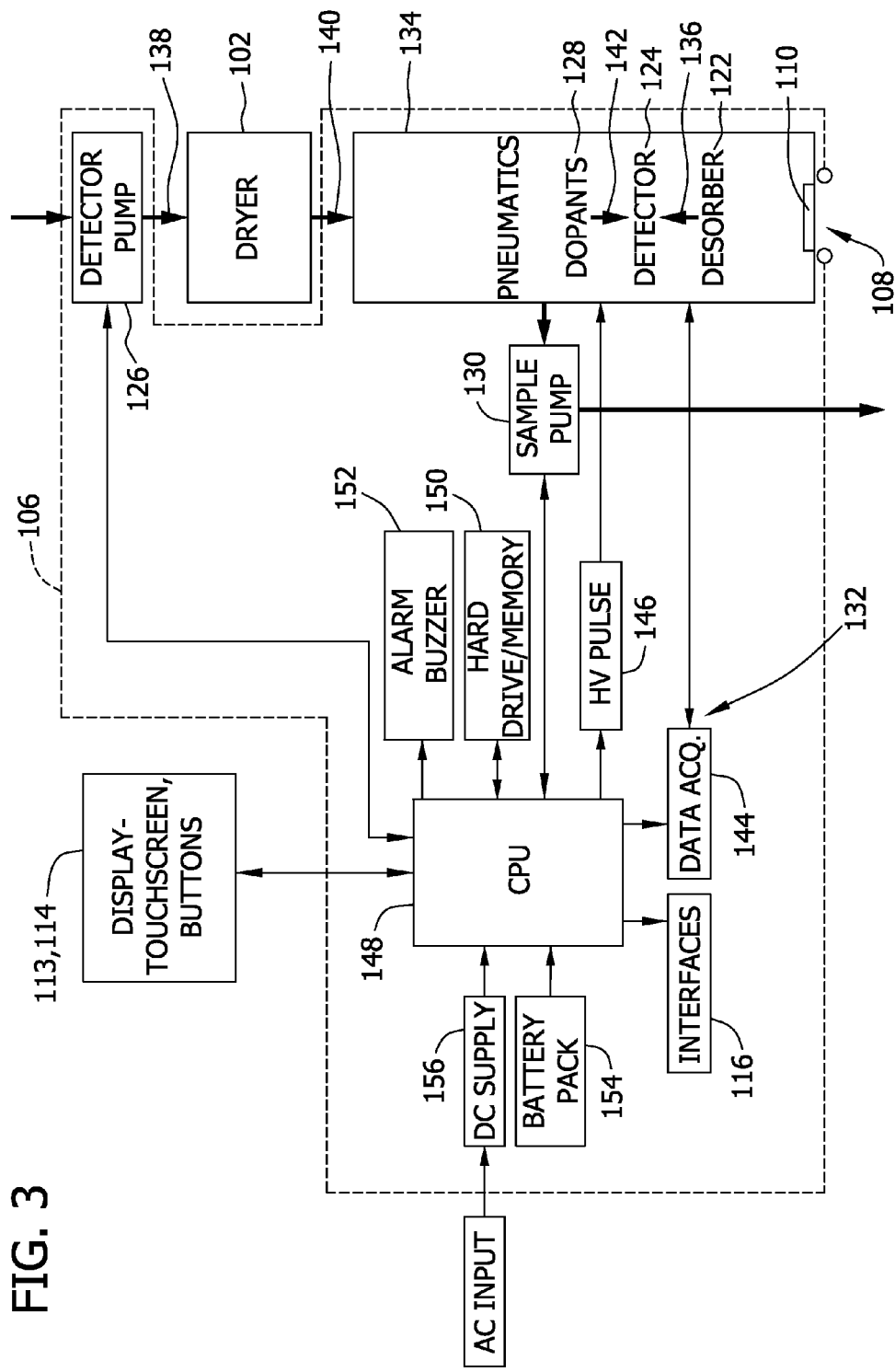

FIG. 1 is a perspective view of an exemplary detection system assembly 100. FIG. 2 is a blown-up perspective view of detection system assembly 100 with a dryer cartridge 102 removed from a detector system 104. FIG. 3 is a schematic view of detection system assembly 100 shown in FIGS. 1 and 2. Detection system assembly 100 is a membrane-less handheld detector having high sensitivity. Detection system assembly 100 operates in a plurality of different modes and can include a hot-swappable battery. In the exemplary embodiment, detection system assembly 100 weight less than 13 pounds (lbs), and more particularly less than 10 lbs, and in a particular embodiment, less than 7 lbs.

Detection system assembly 100 includes detector system 104 and dryer cartridge 102 removably coupled to detector system 104. More specifically, detector system 104 is enclosed within a housing 106, and dryer cartridge 102 is removably coupled to housing 106 to interact with detector system 104. Housing 106 is sealed such that components within housing 106 do not contact ambient air surrounding detection system assembly 100. However, housing 106 includes an opening 108 that allows access to a sample port 110 of detector system 104. More specifically, opening 108 is configured to receive a sample trap (not shown) to be analyzed by detector system 104.

Housing 106 includes a chamber or recess 111 defined therein. More specifically, recess 111 is defined by an outer surface 112 of housing 106 to facilitate isolating the components within housing 106 from the ambient air. Recess 111 is configured to receive dryer cartridge 102 therein when dryer cartridge 102 is coupled to housing 106. As such, dryer cartridge 102 is removably coupled to outer surface 112 of housing 106. Outer surface 112 defines an inlet (not shown) and an outlet (not shown) that provide flow communication between detector system 104 and dryer cartridge 102 when dryer cartridge 102 is coupled to outer surface 112.

In an alternative embodiment, housing 106 does not include recess 111, but dryer cartridge 102 is still removably coupled to outer surface 112 of housing 106 to facilitate easy access to dryer cartridge 102 coupled to detector system 104. In the exemplary embodiment, recess 111 is not covered; however, it should be understood that housing 106 can include a cover (not shown) configured to open and close recess 111. When housing 106 includes the cover, the cover can be configured to isolate components within housing 106 from the ambient air such that recess 111 does not need to be defined by outer surface 112, rather, recess 111 can be defined in outer surface 112. In such an embodiment, dryer cartridge 102 is removably coupled to detector system 104 within housing 106.

Further, housing 106 includes a display 113, navigation buttons 114, interfaces 116, and a handle 118. Display 113 is, for example, a screen configured to display text and/or graphics to a user of detection system assembly 100. Navigation buttons 114 are configured to enable user interaction with display 113 for selecting options and/or accessing menus displayed on display 113 and/or activating or deactivating detection system assembly 100. Although buttons 114 are shown as hard buttons adjacent display 113, buttons 114 can be soft buttons displayed on a touch screen of display 113. As used herein, the term "adjacent" refers to at least two components and/or surfaces that are in direct contact with each other and/or positioned side-by-side in spaced relation to each other.

Interfaces 116 are configured to electronically transfer information to detection system assembly 100 from another system, such as a computer, and/or from detection system assembly 100 to another system, such as a computer and/or a printer. Interfaces 116 can include, for example, a USB interface, a firewire interface, an Ethernet interface, a serial interface, a parallel interface, a network interface, and/or any suitable electronic interface. Handle 118 is configured to allow the user to easily carry detection system assembly 100 and/or to hold detection system assembly 100 during a sample analysis. Housing 106 also includes an access door 120 that enables access to components of detector system 104 when removed or opened.

Referring to FIG. 3, detector system 104 includes components positioned within housing 106 (shown in FIGS. 1 and 2). More specifically, detector system 104 includes sample port 110, a desorber 122, a detector 124, a detector pump 126, a dopant supply 128, a sample pump 130, and a control system 132. When dryer cartridge 102 is coupled to housing 106, dryer cartridge 102 acts as a dryer of detector system 104. Further, desorber 122, detector 124 dopant supply 128, and pneumatics form a detector assembly 134. Sample port 110 is positioned adjacent to housing opening 108 and is configured to receive a trap having a sample of a substance thereon and/or therein. As such, sample port 110 is configured to receive a sample of an unknown substance. In an alternative embodiment, detector system 104 draws in a sample entrained in an air flow rather than using a trap having the sample therein and/or thereon.

In the exemplary embodiment, desorber 122 includes or is positioned adjacent to sample port 110 and is configured to receive at least a portion of the trap. When the trap is at least partially positioned within desorber 122, desorber 122 is configured to heat the trap to free the collected sample from the trap. Detector 124 includes or is positioned adjacent to desorber 122 and is configured to receive freed sample 136 from desorber 122. Detector assembly 134 can include a nozzle (not shown) and/or a filter (not shown) that can be positioned between desorber 122 and detector 124. In the exemplary embodiment, detector 124 is in flow communication with desorber 122, sample port 110, and the ambient. Detector 124 is, in the exemplary embodiment, an ion mobility spectrometer and/or an ion trap mobility spectrometer.

Sample pump 130 is coupled in flow communication with detector assembly 134 and control system 132. As such, sample pump 130 is in flow communication with the ambient via detector assembly 134. When activated in, for example, a sampling mode, sample pump 130 draws air into detector assembly 134 from the ambient air outside of sample port 110. As such, the air is drawn through desorber 122 into detector 124 to draw freed sample 136 into detector 124. Freed sample 136 is channeled or directed from detector 124 to the ambient through sample pump 130. The flow of air and/or the sample from the ambient, through desorber 122, detector 124, and sample pump 130, to the ambient is referred to herein as a sample circuit or loop. When detector system 104 is inactive, sample loop can be closed, for example, before detector 124 and/or at sample port 110. In a particular embodiment, when detector system 104 is inactive for a predetermined period of time the sample flow circuit is closed.

Detector pump 126 is in flow communication with detector assembly 134 and, more particularly, with desorber 122. When activated in, for example, an idle mode, detector pump 126 is configured to draw air 138 from the ambient and direct the air into dryer cartridge 102, dopant supply 128, detector 124, and desorber 122 through a detector circuit or loop. In a particular embodiment, detector pump 126 filters the air before directing the air into dryer cartridge 102. In the exemplary embodiment, the detector loop is a flow path through dryer cartridge 102, dopant supply 128, detector 124, and desorber 122. As such, detector pump 126 is also in flow communication with dryer cartridge 102 and dopant supply 128 and is configured to discharge air into dryer cartridge 102. Dryer cartridge 102 is described in more detail below. In the exemplary embodiment, dryer cartridge 102 discharges drier air 140 into dopant supply 128. As used herein, the term "drier air" refers to air having a humidity that is less than a humidity of air 138 at an inlet of dryer cartridge 102. Further, although "air" is referred to, it should be understood that an air flow may include other components, such as dopant, vapors, water vapor, particles, particulates, and/or any other suitable components.

Dopant supply 128 is in flow communication with dryer cartridge 102 and is configured to receive drier air 140. Dopant supply 128 is configured to add a dopant to drier air 140 as a charge transfer mediator. More specifically, dopant supply 128 channels or directs doped drier air 142 into detector assembly 134 and, more particularly, into detector 124 and/or desorber 122. Doped drier air 142 acts as a carrier gas to steal charge from unwanted ions from freed sample 136 and channel freed sample 136 from desorber 122 into detector 124. Within desorber 122, the dopant mixes with ambient air and the freed sample, and the dopant, the freed sample, ambient air, and the drier air flow into detector 124. Desorber 122 is configured heat the sample and any ambient air that may be drawn into desorber 122. As such, air discharged from desorber 122 has a higher humidity than a humidity of drier air 140 entering desorber 122 and may include ambient air drawn into sample port 110. Dopant supply 128 and detector pump 126 are in flow communication with sample port 110 via desorber 122.

Control system 132 includes a data acquisition board 144, a high voltage (HV) pulse board 146, a CPU/processor 148, a memory 150, an alarm 152, a battery pack 154, and a direct current (DC) power supply 156. Processor 148 is in communication with detector pump 126, sample pump 130, data acquisition board 144, HV pulse board 146, memory 150, alarm 152, battery pack 154, and DC power supply 156. Further, display 113, buttons 114, and interfaces 116 are in communication with processor 148. In the exemplary embodiment, battery pack 154 is removable from detection system 104 for recharge and/or replacement. Alternatively, battery pack 154 is not removable but can be recharged using, for example, DC power supply 156. In the exemplary embodiment, DC power supply 156 receives AC power and transmits DC power to processor 148.

Data acquisition board 144 is in further communication with detector assembly 134 to receive signals from detector assembly 134. The signals indicate migration times of ionized molecules through detector 124, which varies depending on which chemicals and/or biological material are present in the sample. Data acquisition board 144 transmits the signals to processor 148 for further processing. HV pulse board 146 is in communication with detector assembly 134 to create an electric field required to move ions through detector 124.

Processor 148 is configured to process the signals from data acquisition board 144 to determine a chemical and/or a biological material of the sample within detector 124 and output an indication to the user of whether or not a target chemical and/or target biological material is present in the sample. More specifically, processor 148 is in communication with power supply 154 and/or 156, data acquisition board 144, interfaces 116, memory 150, display 113, and buttons 114. Processor 148 is configured to control operations of detector assembly 134, detector pump 126, and sample pump 130. Processor 148 outputs a status of a test and/or an analysis performed using detector assembly 134 to display 113 and/or interfaces 116. Processor 148 can save test/analysis results, operational data, and/or any other suitable data in memory 150. In the exemplary embodiment, memory 150 can be removable from detector system 104. For example, memory 150 can be a removable or non-removable non-transitory computer-readable medium that includes a computer program having code segments configured to perform the methods described herein. Further, memory 150 and/or processor 148 can communicate with another system, such as a computer and/or a printer, via interfaces 116. Processor 148 is configured to perform any suitable method described below.

Figure 4:
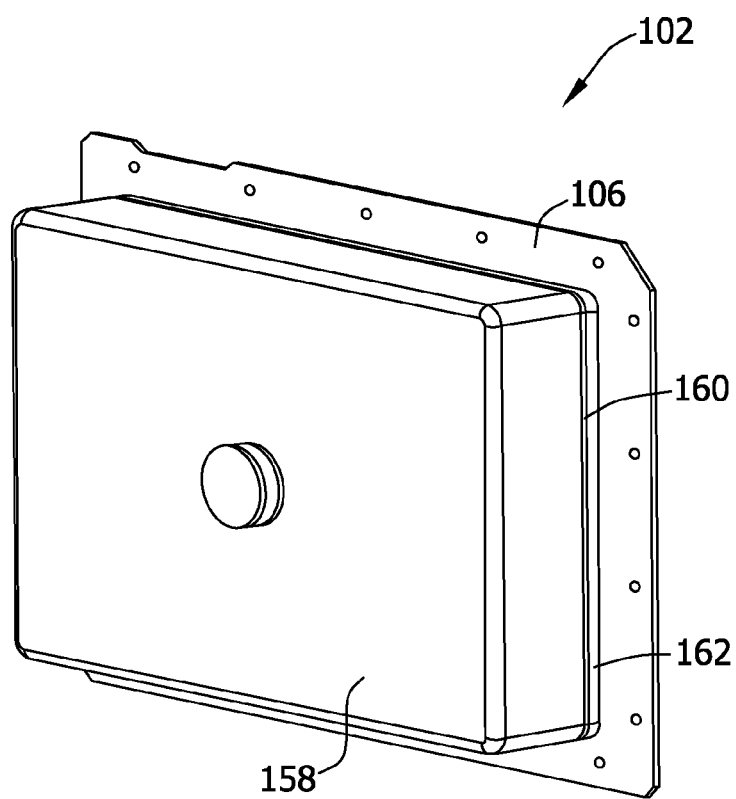
Figure 5:
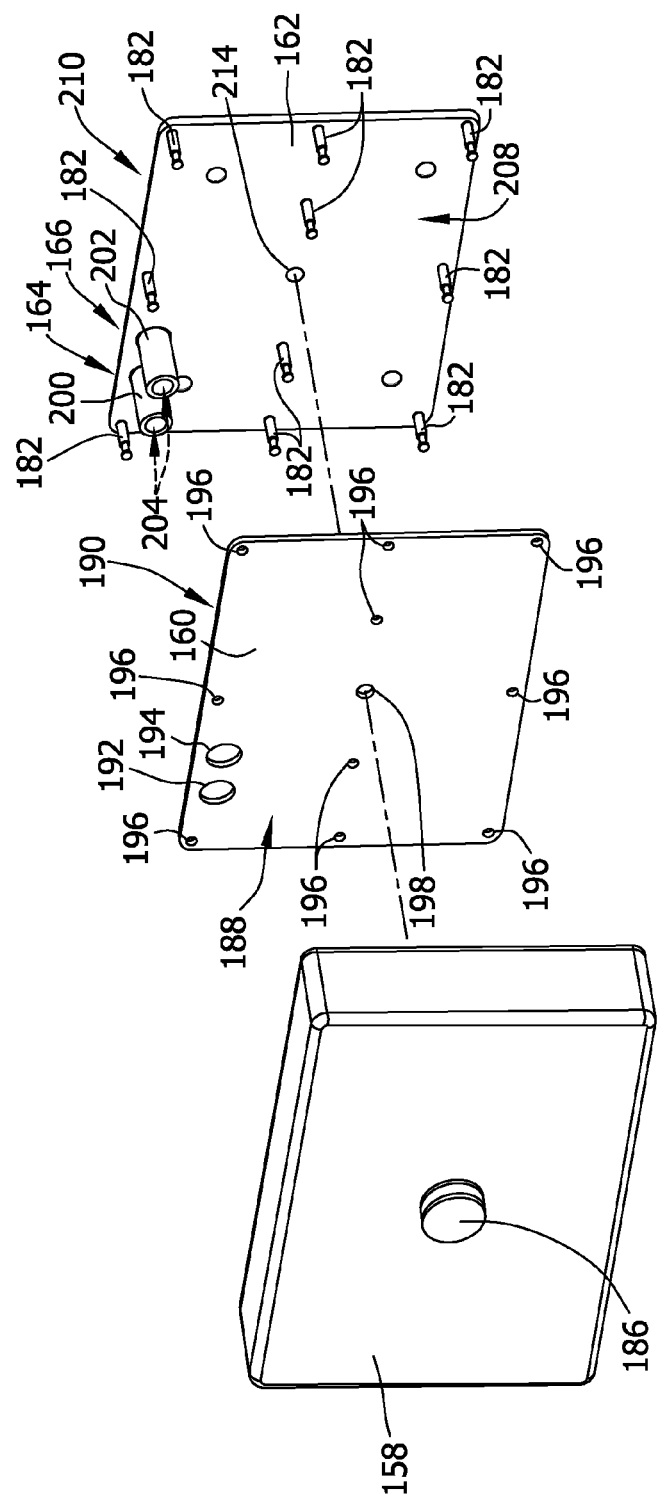
Figure 6:
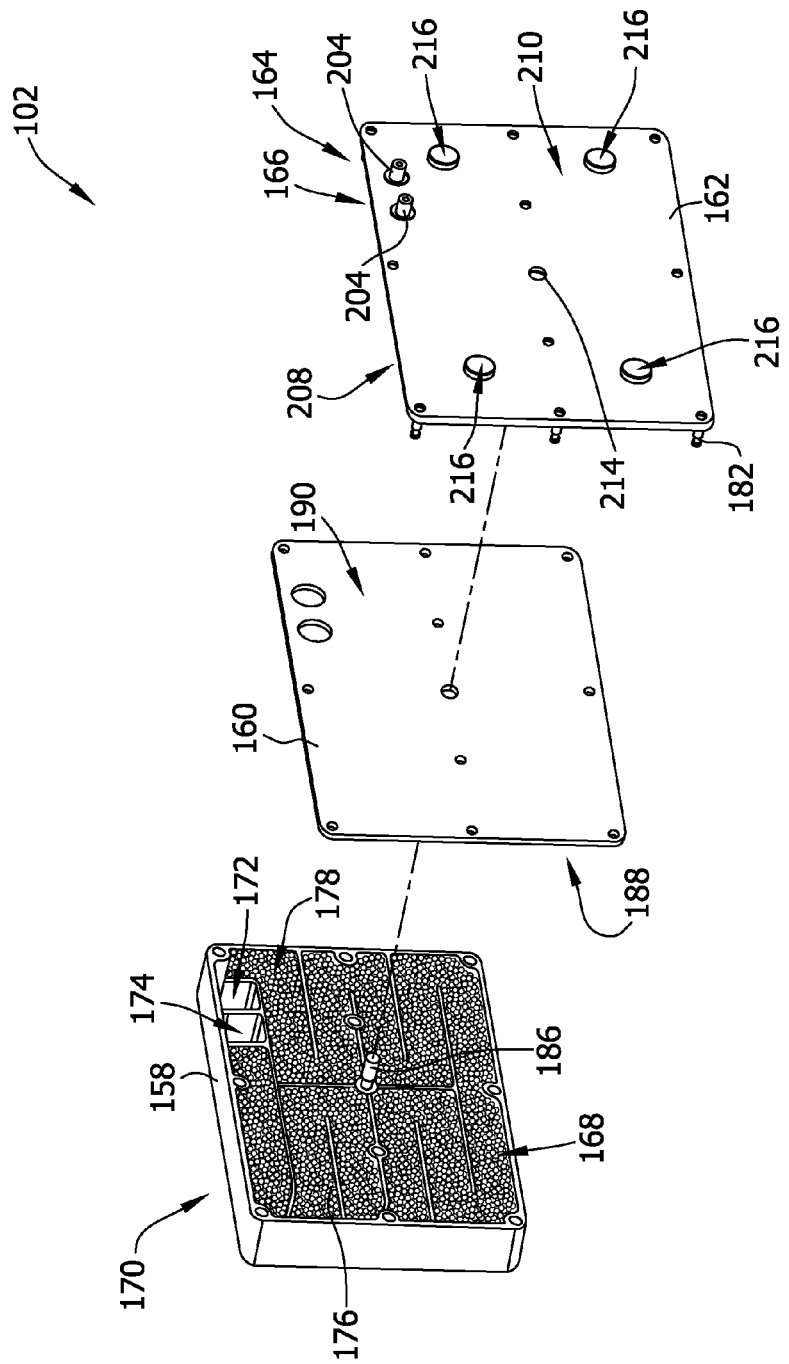
Figure 7:
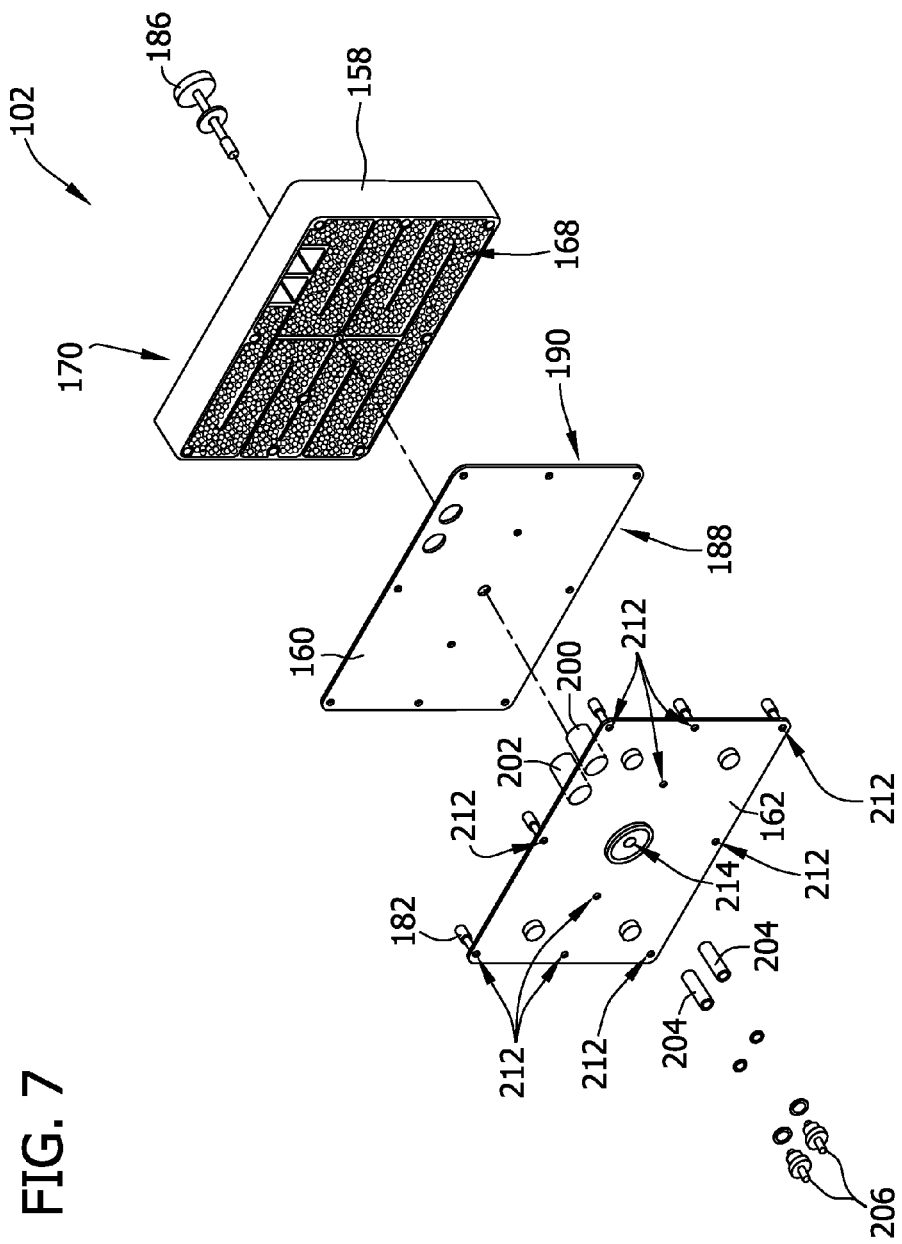
Figure 8:
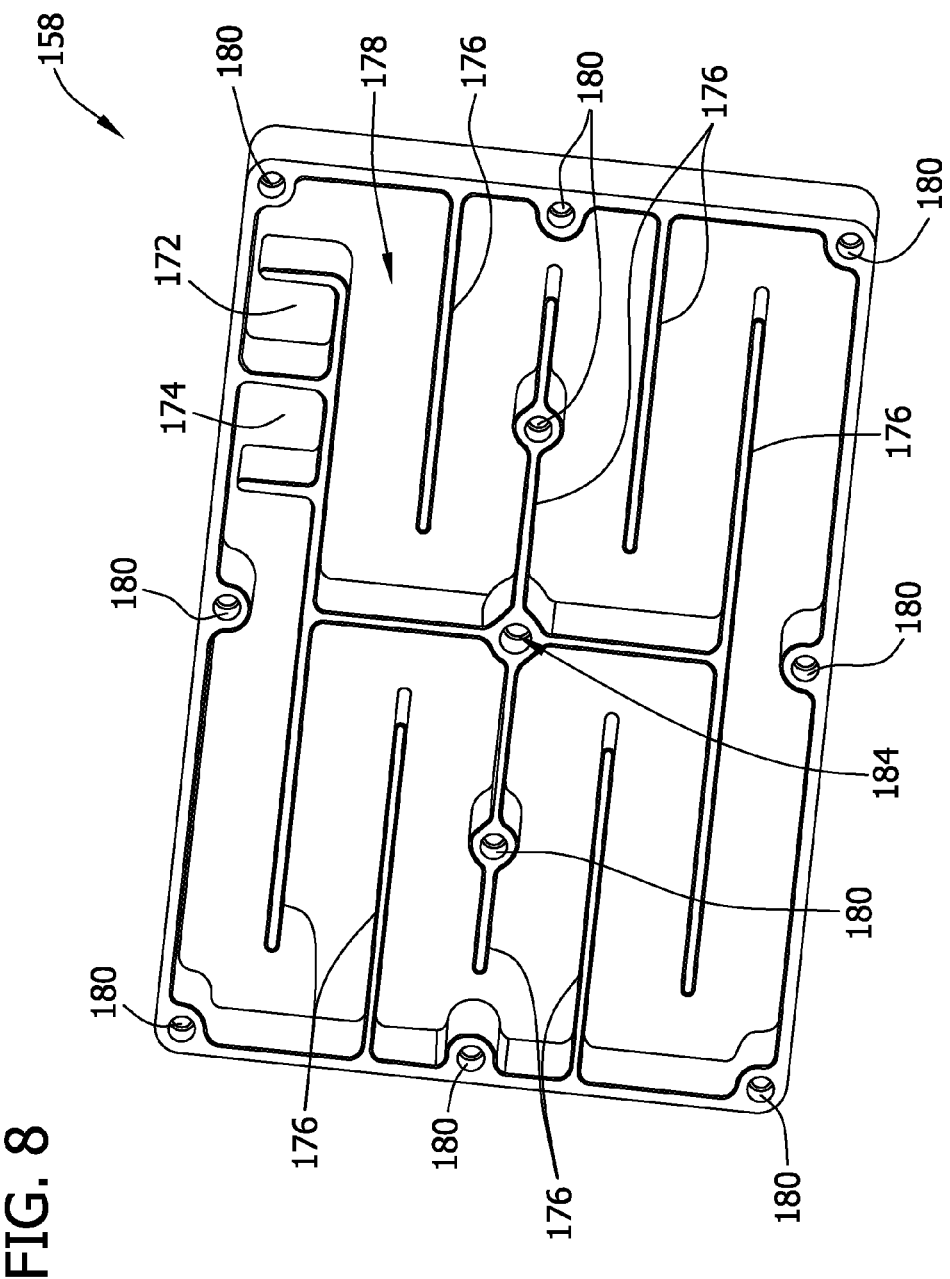

FIG. 4 is a perspective view of an exemplary dryer cartridge 102 that may be used with detection system assembly 100 (shown in FIGS. 1-3) and, more particularly, with detector system 104. FIG. 5 is an exploded front perspective view of dryer cartridge 102. FIG. 6 is an exploded rear perspective view of dryer cartridge 102. FIG. 7 is another exploded rear perspective view of dryer cartridge 102. FIG. 8 is a rear view of an exemplary housing 158 that may be used with dryer cartridge 102. Dryer cartridge 102 is configured to receive the air flow from a first component of detector system 104 (shown in FIGS. 1-3), such as detector pump 126 (shown in FIG. 3), and to discharge the air into at least a second component of detector system 104, such as, dopant supply 128 (shown in FIG. 3), when dryer cartridge 102 is coupled to detector system 104.

Dryer cartridge 102 includes housing 158, a gasket 160, and a coupling plate 162 coupled to housing 158 and gasket 160. In the exemplary embodiment, gasket 160 is formed from any suitable material, such as a high-temperature elastomer material. An inlet 164 and an outlet 166 enable a cavity within dryer cartridge 102 to be in flow communication with detector system 104 through coupling plate 162. Inlet 164 is configured to receive an air flow, and outlet 166 is configured to discharge air. In the exemplary embodiment, housing 158 defines a flow path between inlet 164 and outlet 166 and includes a sieve material 168 configured to capture liquid particles and/or vapor from the air flow through inlet 164. More specifically, an air flow enters dryer cartridge 102 through inlet 164 from detector pump 126 (shown in FIG. 3), and drier air 140 (shown in FIG. 3) is discharged from dryer cartridge 102 through outlet 166 to detector assembly 134 (shown in FIG. 3). Sieve material 168 is configured to reduce an amount of liquid vapors and/or liquid particles in the air flow entering dryer cartridge 102 to discharge the drier air. Sieve material 168 includes any suitable material that captures liquid particles and/or vapors from the air flow. In the exemplary embodiment, sieve material 168 includes a molecular sieve material.

A capture portion 170 includes housing 158 and sieve material 168. Housing 158 is coupled to gasket 160 and coupling plate 162 such that sieve material 168 is enclosed between housing 158 and gasket 160. More specifically, gasket 160 is configured to form an air-tight seal about housing 158 to enclose sieve material 168 within housing 158. As such, gasket 160 is configured to isolate a cavity of capture portion 170 from ambient conditions. As shown in FIG. 8, housing 158 includes an inlet chamber 172, an outlet chamber 174, and a plurality of baffles 176 extending into a cavity 178 of housing 158. Inlet chamber 172 is configured to align with inlet 164, and outlet chamber 174 is configured to align with outlet 166 when coupling plate 162 is coupled to housing 158. Baffles 176 define a flow path between inlet chamber 172 and outlet chamber 174. Sieve material 168 is positioned between baffles 176 to capture liquid particles and/or liquid vapors as the air flow is channeled or directed through dryer cartridge 102. A plurality of fastener apertures 180 are defined in housing 158 and are configured to receive a fastener 182 (shown in FIG. 5) to couple housing 158 to coupling plate 162. Further, at least one coupling aperture 184 is defined in housing 158 and is configured to receive a coupling fastener 186 to couple dryer cartridge 102 to detector system 104. In the exemplary embodiment, baffles 176, fastener apertures 180, and coupling aperture 184 are formed integrally as one piece with housing 158.

Gasket 160 includes a first side 188 and a second side 190. An inlet aperture 192, an outlet aperture 194, a plurality of fastener apertures 196, and at least one coupling aperture 198 are defined though sieve between first side 188 and second side 190. Inlet aperture 192 is configured to align with inlet 164 and inlet chamber 172, and outlet aperture 194 is configured to align with outlet 166 and outlet chamber 174 when capture portion 170 and gasket 160 are coupled to coupling plate 162. When gasket 160 is positioned adjacent housing 158, baffles 176 are adjacent first side 188 of gasket 160. Further, when coupling plate 162 is coupled to housing 158, coupling plate 162 is adjacent second side 190 of gasket 160.

Coupling plate 162 is configured to removably couple capture portion 170 to detector system housing 106 (shown in FIGS. 1 and 2). As such, coupling plate 162 is configured to removably couple dryer cartridge 102 to detector system 104 (shown in FIGS. 1-3). Coupling plate 162 includes inlet 164 and outlet 166 defined therethrough. More specifically, in the exemplary embodiment, inlet 164 includes a first tube 200 extending from coupling plate 162, and outlet 166 includes a second tube 202 extending from coupling plate 162. First tube 200 is configured to extend through sieve inlet aperture 192 and at least partially into inlet chamber 172 when coupling plate 162 is coupled to housing 158. Similarly, second tube 202 is configured to extend through sieve outlet aperture 194 and at least partially into outlet chamber 174 when coupling plate 162 is coupled to housing 158. Tubes 200 and 202 are formed integrally as one piece with coupling plate 162 and/or coupled to coupling plate 162. In the exemplary embodiment, tubes 200 and 202 are partially formed integrally as one piece with coupling plate 162 and partially coupled to coupling plate 162.

A filter 204 is positioned within each tube 200 and/or 202 to filter air entering dryer cartridge 102 and/or being discharged from dryer cartridge 102. Filters 204 are removably coupled within tubes 200 and 202 by, for example, inserting a filter 204 into a respective tube 200 or 202. In a particular embodiment, filter 204 is formed from sintered stainless steel. Further, in the exemplary embodiment, dryer cartridge 102 can include caps 206 configured to couple to first tube 200 and second tube 202 to seal inlet 164 and/or outlet 166 to prevent air from entering dryer cartridge 102.

Coupling plate 162 includes a first side 208 and a second side 210. A plurality of fastener apertures 212 and at least one coupling aperture 214 is defined through coupling plate 162 between first side 208 and second side 210. At least one foot 216 extends from second side 210 of coupling plate 162 to properly align coupling plate 162 with detector system housing 106 and/or to space coupling plate 162 from detector system housing 106.

Figure 9:
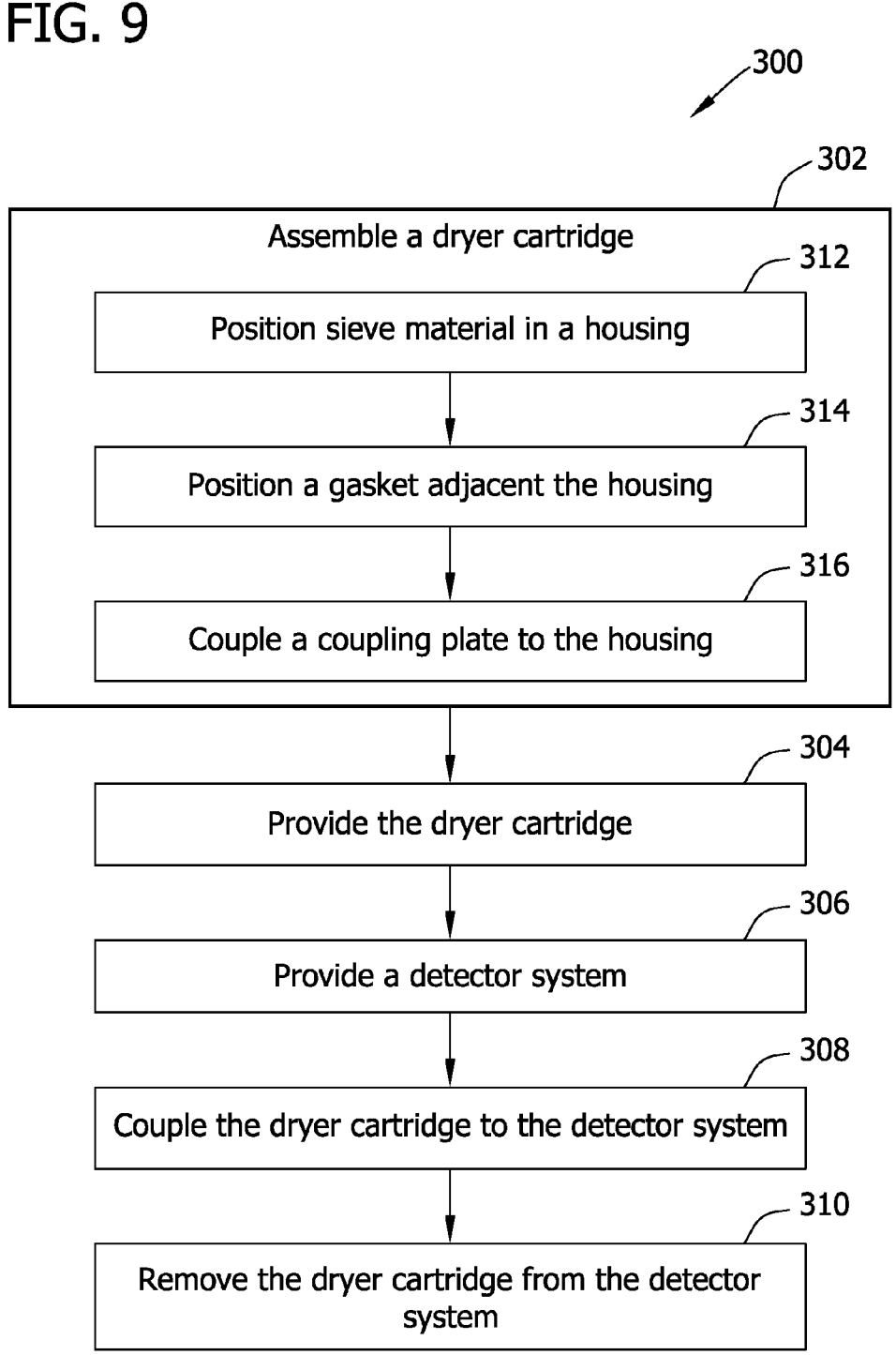

FIG. 9 is a flowchart of an exemplary method 300 for making detection system assembly 100 (shown in FIGS. 1-8). Referring to FIGS. 1-9, method 300 includes assembling 302 dryer cartridge 102, providing 304 dryer cartridge 102, providing 306 detector system 104, and coupling 308 dryer cartridge 102 to detector system 104 to form detection system assembly 100. After a predetermined time period, a predetermined number of uses, upon an alarm, and/or at any other suitable time, dryer cartridge 102 is removed 310 from detector system 104. As used herein, the terms "provide," "providing," and variations thereof refer to supplying, furnishing, preparing, presenting, procuring, purchasing, transferring, producing, manufacturing, fabricating, forging, machining, molding, constructing, and/or any other suitable means to provide a component.

To assemble 302 dryer cartridge 102, sieve material 168 within housing 158. More specifically, sieve material 168 is positioned 312 within the flow path between inlet chamber 172 and outlet chamber 174 defined by baffles 176. Housing 158 and sieve material 168 form capture portion 170. Gasket 160 is positioned 314 adjacent housing 158 and/or sieve material 168. More specifically, first side 188 of gasket 160 is positioned 314 adjacent baffles 176 of housing 158 such that an air-tight seal is formed between sieve material 168 and the ambient air when dryer cartridge 102 is assembled. When gasket 160 is positioned 314 adjacent capture portion 170, inlet aperture 192 is aligned with inlet chamber 172 and outlet aperture 194 is aligned with outlet chamber 174. Coupling plate 162 is then coupled 316 to housing 158 to secure gasket 160 between coupling plate 162 and housing 158. More specifically, fasteners 182 are inserted into and/or through respective plate fastener apertures 212, sieve fastener apertures 196, and housing fastener apertures 180, and fasteners 182 are secured within housing fastener apertures 180. When coupling plate 162 is coupled 316 to housing 158, inlet tube 200 extends through inlet aperture 192 and at least partially into inlet chamber 172, and outlet tube 202 extends through outlet aperture 194 and at least partially into outlet chamber 174. It should be understood that dryer cartridge 102 can also be disassembled once assembled 302. Further, dryer cartridge 102 can be provided 304 assembled or disassembled.

Dryer cartridge 102 is provided 304, and detector system 104 is provided 306 to form detection system assembly 100 by removably coupling 308 dryer cartridge 102 to detector system 104. To couple 308 dryer cartridge 102 to detector system 104, at least one coupling fastener 186 is inserted through housing coupling aperture 184, sieve coupling aperture 198, and plate coupling aperture 214 into a portion of housing 106. Dryer cartridge 102 is positioned adjacent outer surface 112 of housing 106, for example, within recess 111. Coupling fastener 186 is secured to detector system housing 106 to secure dryer cartridge 102 to outer surface 112 of detector system housing 106. To remove 310 dryer cartridge 102 from detector system 104, coupling fastener 186 is uncoupled from detector system housing 106. Coupling fastener 186 can remain coupled to dryer cartridge 102 or can be at least partially removed from dryer cartridge 102. In an alternative embodiment, dryer cartridge 102 is removably coupled 308 to detector system 104 using any suitable mechanism and/or technique.

Figure 10:
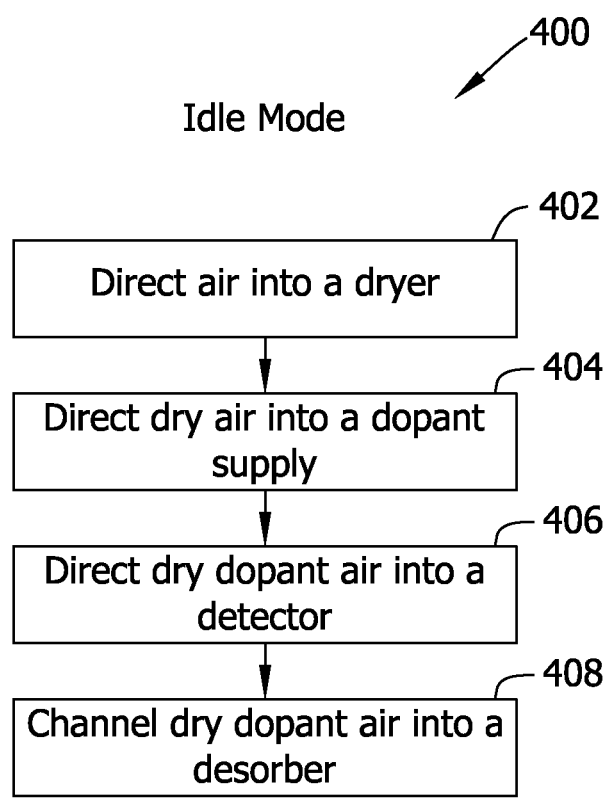

FIG. 10 is a flowchart of an exemplary method 400 for operating detection system assembly 100 (shown in FIGS. 1-8) in an Idle Mode. Method 400 is used to circulate dry dopant gas through detector 124 and desorber 122 to ensure that system assembly 100 has the proper chemistry when a sample is introduced. Referring to FIGS. 1-8 and 10, method 400 includes activating detector pump 126 to channel or direct 402 air 138 from the ambient into dryer cartridge 102. In a particular embodiment, air 138 is filtered before it is directed 402 into dryer cartridge 102. From dryer cartridge 102, the air 140 is channeled or directed 404 into dopant supply 128 to dope the air 140. The doped air 142 is channeled or directed 406 into detector 124 and then directed 408 into desorber 122. The doped air 142 steals charge from unwanted ions with lower charge affinity.

Figure 11:
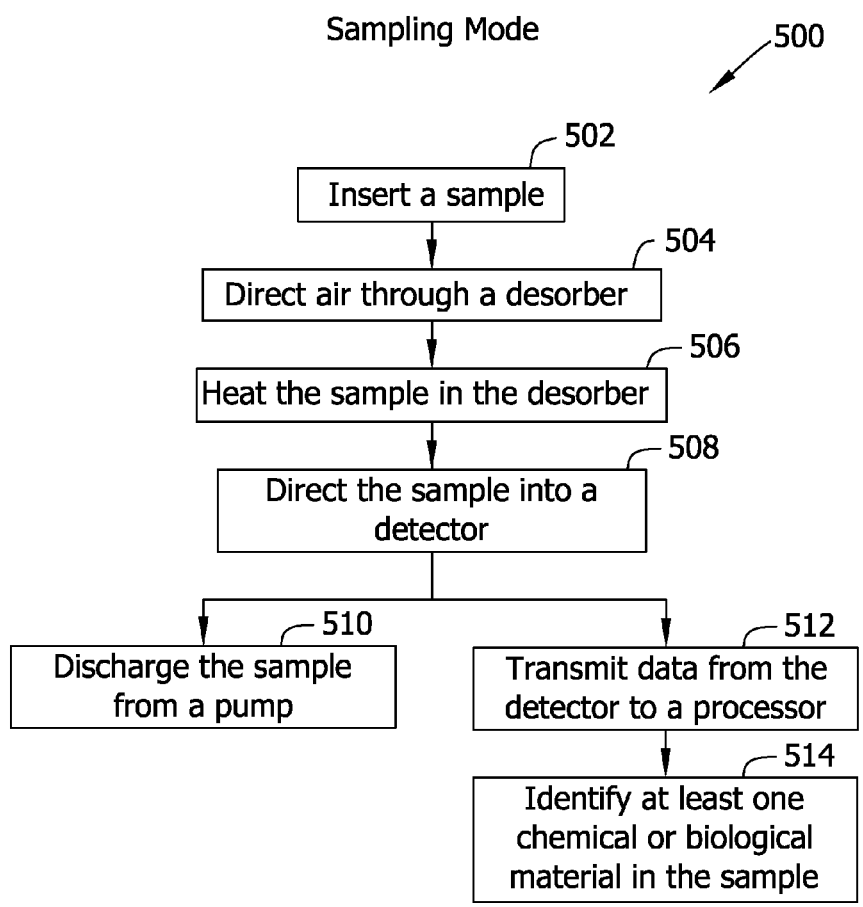

FIG. 11 is a flowchart of an exemplary method 500 for operating detection system assembly 100 (shown in FIGS. 1-8) in a Sampling Mode. Method 500 is used to identify at least one chemical and/or biological material in a sample of a substance. Referring to FIGS. 1-8 and 11, method 500 includes collecting the sample and inserting 502 the sample into detection system assembly 100. For example, the sample is collected on and/or in a trap and inserted 502 into detection system assembly 100 through opening 108 into sample port 110. Alternatively, the sample is collected and inserted 502 by drawing air into detection system assembly 100. In the exemplary embodiment, the sample of the substance is inserted 502 into detector assembly 134 and, more particularly into desorber 122 through sample port 110.

In the exemplary embodiment, detector system 104 is activated and air is channeled or directed 504 through desorber 122. When a sample is introduced, a sample pump activates and draws air from an inlet of desorber 122 and from a detector pump via dryer cartridge 102 and a dopant tube. The collected sample is inserted 502 into detector assembly 134 where the sample is heated 506 by desorber 122. Further, within desorber 122, the sample is freed from the trap by the heat and is mixed with the doped air. The freed sample, the dopant, ambient air, and/or the carrier gas are channeled or directed 508 into detector 124 by sample pump 130. Molecules of the sample interact with components of detector 124 to generate a signal indicative of which molecules are present within the sample. The sample, the dopant, and/or air is discharged 510 from sample pump 130.

The signals are transmitted 512 from detector 124 to processor 148 to identify the molecules of the sample. For example, processor 148 identifies 514 at least one chemical and/or biological material within the sample. Processor 148 displays the identification on display 113, outputs the identification via interfaces 116, and/or issues an alarm if the molecules are molecules of a target material. The alarm can be audio and/or visual. Further, processor 148 display a status of detection system assembly 100 in display 113.

Processor 148 also determines whether dryer cartridge 102 has been wetted during the Idle Mode and/or during the Sampling Mode. More specifically, processor 148 determines whether dryer cartridge 102 has a concentration of liquid that is more than a liquid concentration threshold, dryer cartridge 102 has been used to perform a predetermined number of analyses, dryer cartridge 102 has been used for a predetermined length of time, and/or using any other suitable indicator of the wetness of dryer cartridge 102. The determination can alternatively or additionally be performed manually by a user and/or by a separate system, such as a separate computer. Dryer cartridge 102 is replaced when it is determined that dryer cartridge 102 has been wetted. More specifically, dryer cartridge 102 is replaced by removing dryer cartridge 102 from detector system 104. When dryer cartridge 102 is replaced, another dry dryer cartridge 102 is coupled to detector system 104, as described with respect to FIG. 9. The wetted dryer cartridge 102 can be dried in a separate, external regenerator, such as regenerator 600 shown in FIGS. 12-14. Dryer cartridge 102 continues to be used when it is determined that dryer cartridge 102 has not been wetted.

Figure 12:
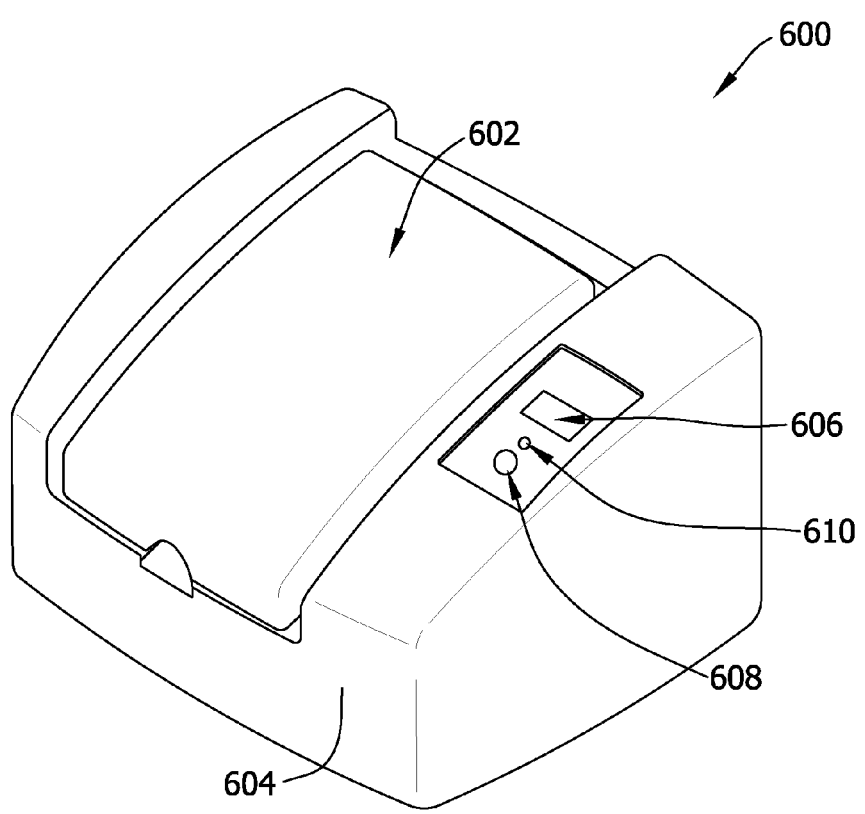
Figure 13:
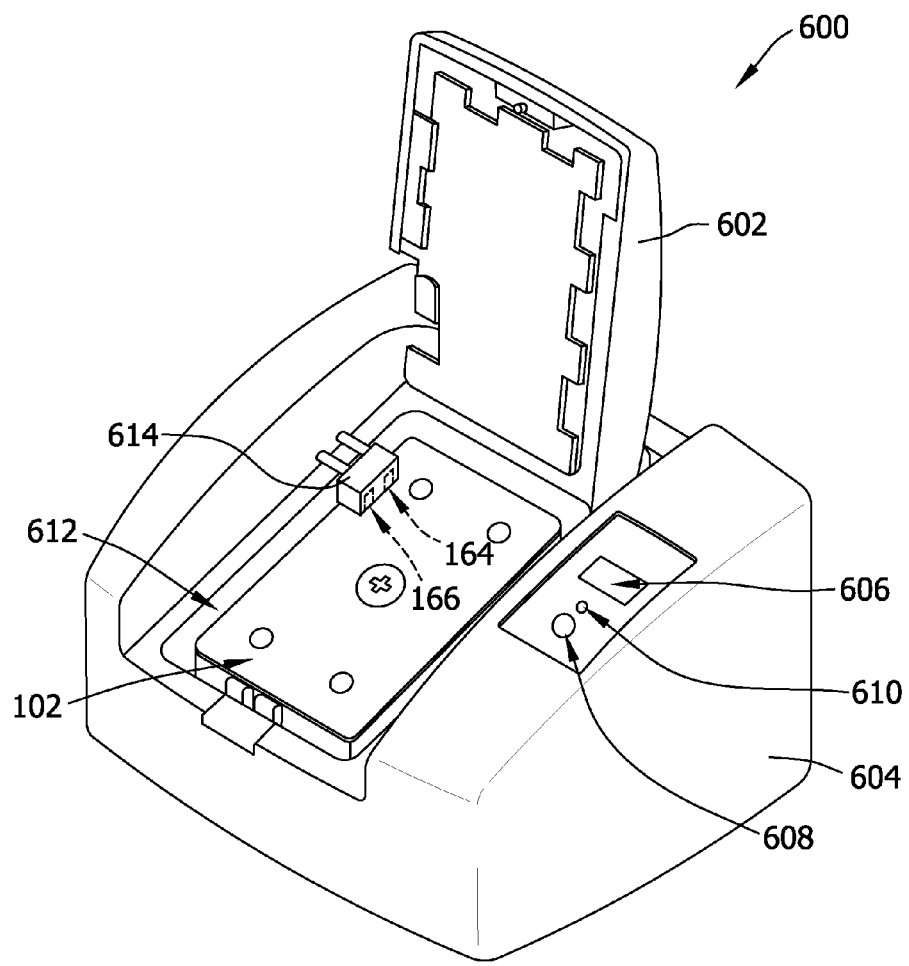
Figure 14:
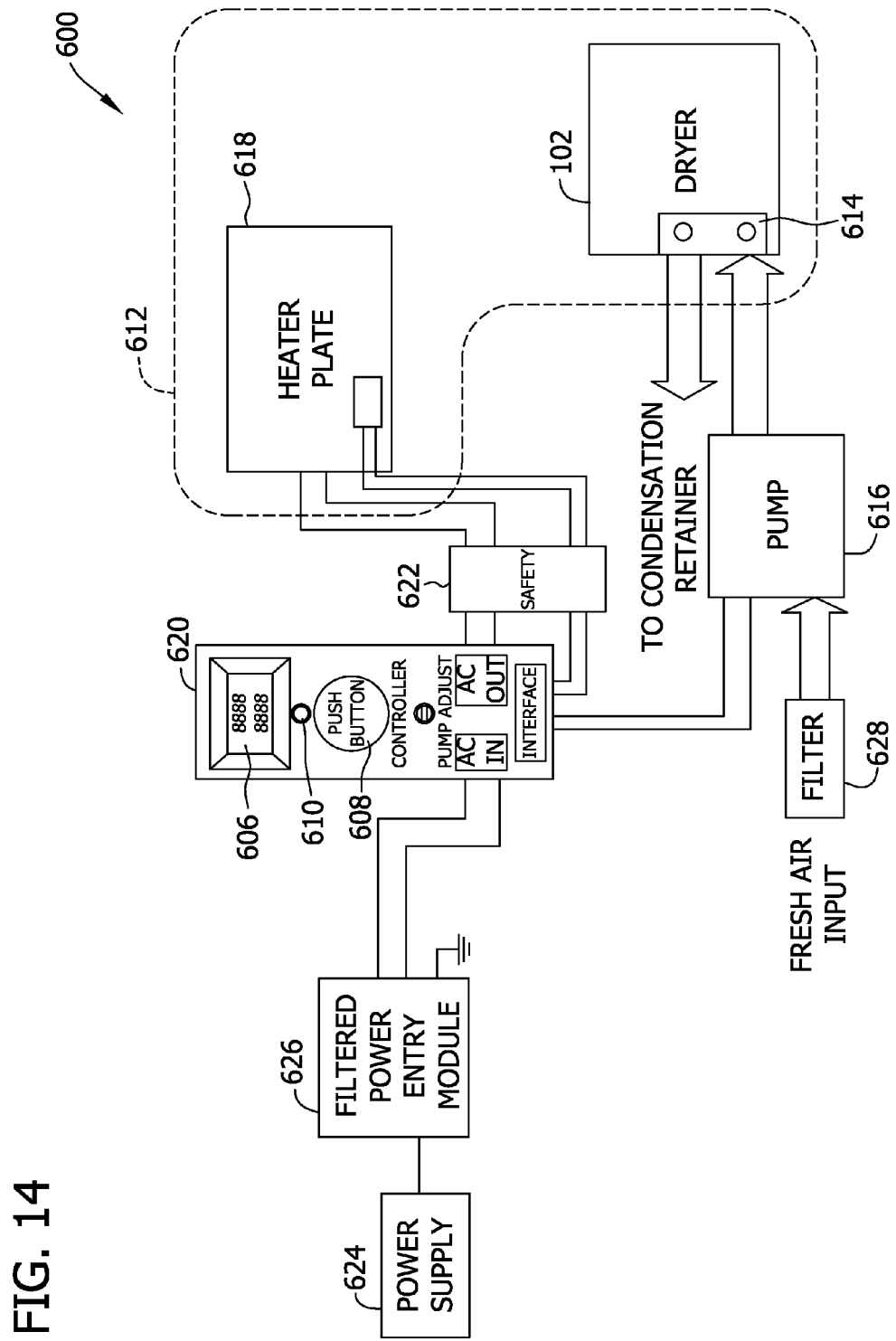

FIG. 12 is a front perspective view of an exemplary regenerator 600 that may be used with dryer cartridge 102 (shown in FIGS. 1-8) with a cover 602 in a closed position. FIG. 13 is a front perspective view of regenerator 600 with cover 602 in an open position. FIG. 14 is a schematic view of regenerator 600. Regenerator 600 is external and separate from detection system assembly 100 (shown in FIGS. 1 and 2), but can be supplied with detection system assembly 100. As such, regenerator 600 can be stored and/or used separately from detection system assembly 100.

Regenerator 600 includes a housing 604 having cover 602 rotatably coupled thereto. Housing 604 includes a display 606, at least one button 608, and a visual indicator 610. Display 606 is configured to display at least a status of a drying operation of regenerator 600. Button 608 is configured to enable a user to control regenerator 600 and/or interact with display 606. Although button 608 is shown as a hard button adjacent display 606, button 608 can be a soft button displayed on a touch screen of display 606. Visual indicator 610 is, for example, a light-emitting diode (LED), which is controllable to be continuously lighted and/or periodically lighted. In particular embodiments, visual indicator 610 includes a red LED, an amber LED, and/or a green LED. Housing 604 further includes a chamber 612 defined adjacent cover 602 such that cover 602 can isolate chamber 612 from the surrounding environment and/or ambient conditions. Chamber 612 is configured to receive at least a portion of dryer cartridge 102.

Referring to FIG. 13, a flow connector 614 extends into chamber 612 and is in flow communication with components, such as a pump 616 and/or a condensation retainer (not shown), within housing 604. Flow connector 614 is configured to removably couple in flow communication with inlet 164 and outlet 166 of dryer cartridge 102. In a particular embodiment, flow connector 614 snaps on to tubes 200 and 202 (both shown in FIGS. 5-7) and is secured to tubes 200 and 202 by a friction fit. Alternatively, flow connector 614 uses any suitable technique and/or components to removably couple to dryer cartridge 102. In the exemplary embodiment, flow connector 614 is configured to direct air from pump 616 into dryer cartridge 102 through inlet 164 and to channel air and/or vapors discharged from dryer cartridge 102 through outlet 166 into the condensation retainer.

Referring to FIG. 14, regenerator 600 further includes pump 616, a heater 618, and a controller 620 positioned within housing 604. A temperature sensor (not shown) can be associated with heater 618 and in communication with controller 620, and a pressure sensor (not shown) can be associated with pump 616 and in communication with controller 620. At least one button 608, such as a start/stop button and/or a timer set button, is in communication with controller 620 for inputting data to controller 620. Controller 620 is further in communication with display 606, a safety controller 622, and a power supply 624. Safety controller 622 is in communication with the temperature sensor and/or heater 618. Power supply 624 is any suitable supply that provides power to regenerator 600 and can be in communication with a filtered power entry module 626.

Heater 618 is positioned within housing 604 adjacent chamber 612 and is configured to heat dryer cartridge 102 when dryer cartridge 102 is positioned within chamber 612. In the exemplary embodiment, heater 618 includes a heat plate that is positioned adjacent a bottom wall of chamber 612 such that heater 618 is in chamber 612. As such, heater 618 is configured to contact at least a portion of dryer cartridge 102 and/or to support dryer cartridge 102 thereon. The temperature sensor is configured to measure a temperature of heater 618 and/or dryer cartridge 102. The temperature sensor is further configured to transmit the measured temperature to safety controller 622 and controller 620. Safety controller 622 is configured to turn heater 618 off when the measured temperature exceeds a maximum temperature threshold, as described in more detail below.

Pump 616 is positioned within housing 604 adjacent an air intake opening (not shown) defined through housing 604. Pump 616 is configured to draw air from the ambient and discharge air into dryer cartridge 102 positioned in chamber 612 via flow connector 614. As such, a flow of air is channeled or directed through dryer cartridge 102 within chamber 612 using pump 616. A filter 628 can be positioned upstream of pump 616 and/or dryer cartridge 102 to remove particles and/or vapors from the ambient air before the air is channeled or directed through pump 616 and/or dryer cartridge 102. Filter 628 can be replaceable. The pressure sensor is configured to measure a pressure of air within pump 616 and/or air being discharged from pump 616. The pressure sensor is further configured to transmit the measured pressure to controller 620.

Controller 620 is in communication with heater 618 and pump 616 to control a temperature of heater 618, a rate of the flow of air discharged from pump 616, a heating time, a cooling time, and/or any other suitable operation and/or parameter of regenerator 600. Controller 620 is configured to receive an on/off signal from a user via button 608. When regenerator 600 is on, controller 620 is configured to control heater 618 and pump 616 to heat dryer cartridge 102 while pumping ambient air through dryer cartridge 102. In the exemplary embodiment, controller 620 is configured to perform the methods and/or steps described in more detail below.

More specifically, heater 618 is controlled to heat dryer cartridge 102 to a predetermined temperature and/or predetermined temperature range for a predetermined time period. This predetermined time period is referred to as a drying cycle. Heater 618 can be activated and deactivated during the drying cycle to maintain a temperature of dryer cartridge 102 within the predetermined temperature range during the drying cycle. At the end of the drying cycle, controller 620 is configured to deactivate heater 618 and pump 616. When the temperature of dryer cartridge 102 exceeds the maximum temperature threshold, controller 620 and/or safety controller 622 is configured to deactivate heater 618, pump 616, and/or regenerator 600.

Further, during the drying cycle, controller 620 is configured to control pump 616 to channel or direct an air flow through dryer cartridge 102 at a predetermined flow rate and/or predetermined flow rate range. The air flow rate can be automatically controlled by controller 620 and/or manually adjustable. A pressure measurement from the pressure sensor indicates the air flow rate. In the exemplary embodiment, controller 620 is configured to turn pump 616 off when the flow rate is less than a minimum air flow rate or when the flow rate is more than a maximum air flow rate. More specifically, a low air flow rate indicates that filter 628 and/or pump 616 is fouled or otherwise has a reduced flow rate. A high air flow rate indicates that dryer cartridge 102 is not present within chamber 612.

During the heating cycle, controller 620 is configured to activate visual indicator 610 to be continuously lighted. During a cooling cycle following the heating cycle, controller 620 is configured to activate visual indicator 610 to be periodically lighted. The cooling cycle is a period of time that enables dryer cartridge 102 to cool to a predetermined temperature at which a user can handle dryer cartridge 102. After the cooling cycle, controller 620 is configured to deactivate visual indicator 610. Alternatively or additionally, controller 620 can display a status of the heating cycle, the cooling cycle, heater 618, pump 616, and/or any other suitable operation of regenerator 600 textually or graphically using display 606.

In the exemplary embodiment, a detection kit includes detector system 104 (shown in FIGS. 1-3), at least two dryer cartridges 102, and regenerator 600. As such, while a first dryer cartridge 102 is coupled to detector system 104, a second dryer cartridge 102 can be dried in regenerator 600 or stored with caps 206 (shown in FIG. 7) on inlet 164 and outlet 166 (both shown in FIG. 5).

Figure 15:
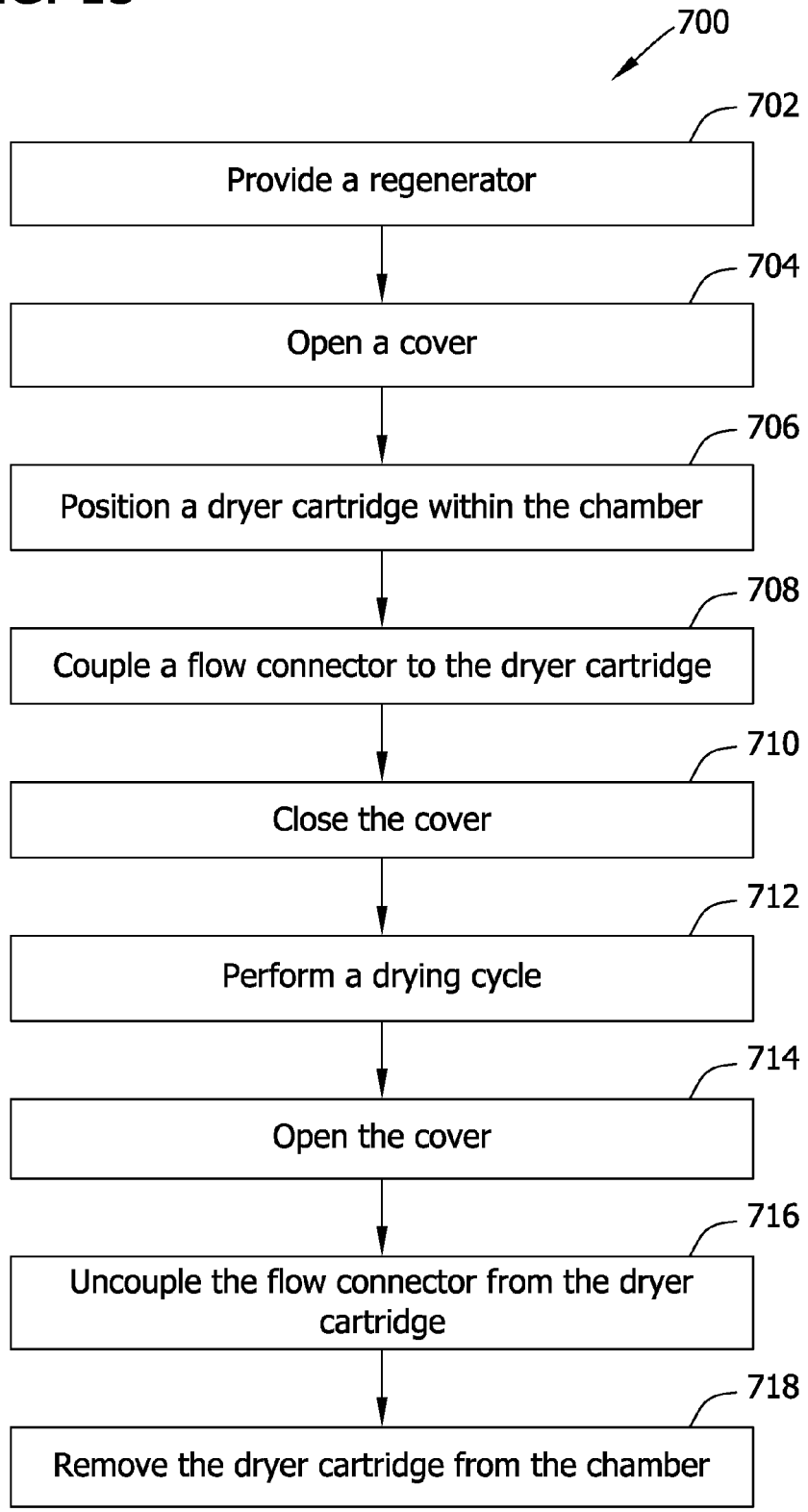

FIG. 15 is a flowchart of an exemplary method 700 for using regenerator 600 (shown in FIGS. 12-14). Method 700 is used to dry a dryer cartridge 102 (shown in FIGS. 1-8) from a first concentration, such as a concentration of at least 30,000 parts-per-million by volume (ppmv) $H_2O$, to a second lower concentration, such as a concentration of less than 500 ppmv $H_2O$ and more particularly to less than 100 ppmv $H_2O$, within a predetermined time period. Referring to FIGS. 12-15, method 700 includes providing 702 regenerator 600, and opening 704 cover 602 to provide access to chamber 612, and positioning 706 dryer cartridge 102 within chamber 612.

In the exemplary embodiment, dryer cartridge 102 is positioned with respect to, such as on, heater 618 and in flow communication with pump 616. More specifically, flow connector 614 is removably coupled 708 to dryer cartridge 102 to provide flow communication between pump 616 and dryer cartridge 102 and/or between the condensation retainer and dryer cartridge 102. Cover 602 is closed 710 to isolate chamber 612 from the surrounding environment and/or ambient conditions during the drying cycle. The drying cycle is performed 712 automatically when the user closes 710 cover 602 and/or manually upon activation of button 608. The drying cycle includes the heating cycle and the cooling cycle, which are described in more detail with respect to FIG. 16. When the drying cycle finishes, the user opens 714 cover 602 and uncouples 716 flow connector 614 from dryer cartridge 102. Dryer cartridge 102 is then removed 718 from chamber 612. Dryer cartridge 102 is coupled to detector system 104 (shown in FIGS. 1-3) or caps 206 (shown in FIG. 7) are coupled to dryer cartridge 102, as described in more detail above.

Figure 16:
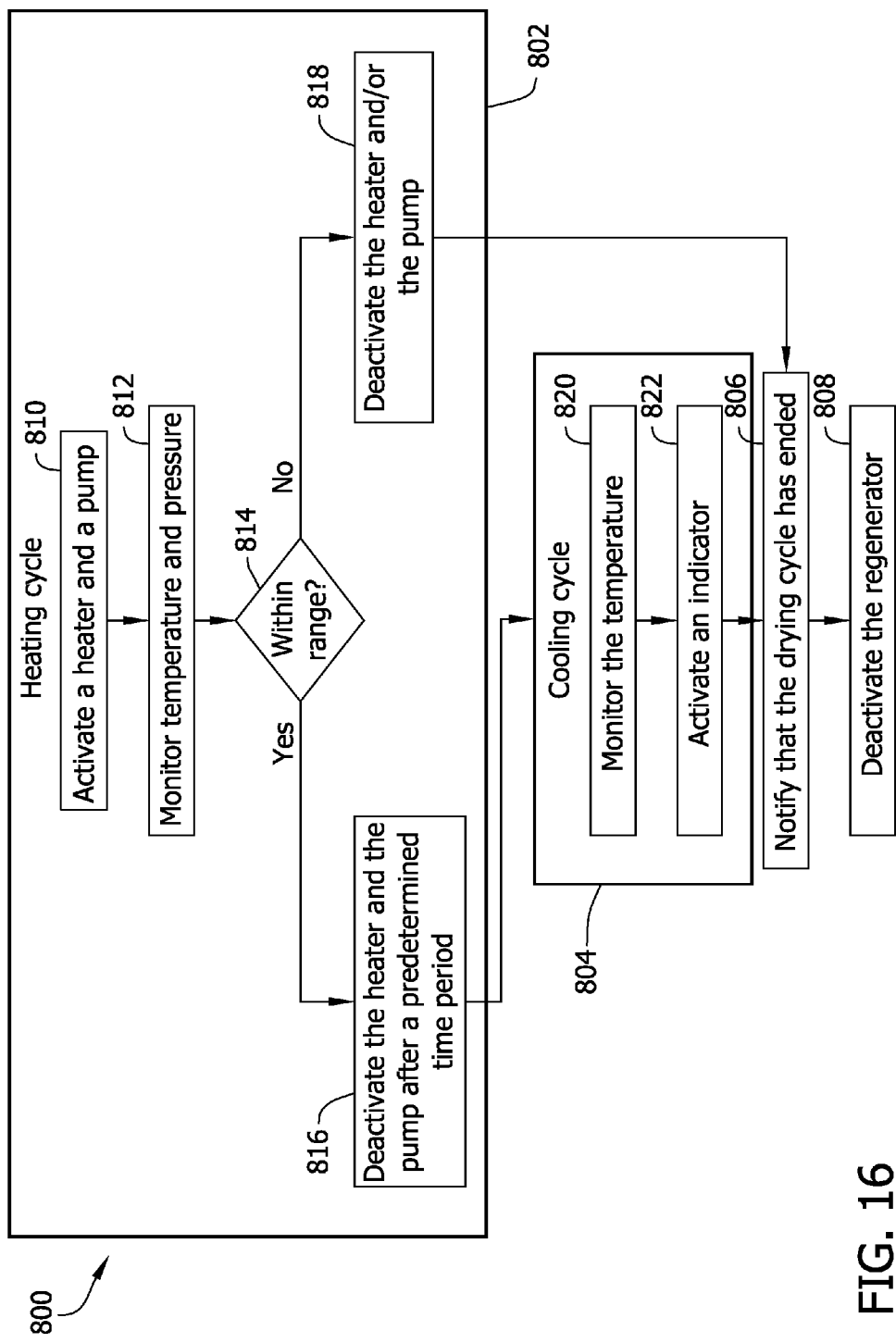

FIG. 16 is a flowchart of an exemplary method 800 of operating of regenerator 600 (shown in FIGS. 12-14). Method 800 is performed by controller 620 (shown in FIG. 14) to dry a dryer cartridge 102 (shown in FIGS. 1-8) positioned within regenerator 600. In the exemplary embodiment, method 800 is performed as step 712 shown in FIG. 15. As such, method 800 performs an exemplary drying cycle that includes a heating cycle and a cooling cycle.

Referring to FIGS. 12-14 and 16, method 800 includes performing 802 a heating cycle and performing 804 a cooling cycle. After the cooling cycle is performed 804, a user is notified 806 that the drying cycle has ended. For example, controller 620 deactivates visual indicator 610 and/or textually and/or graphically displays a notification using display 606 when the drying cycle has ended. Regenerator 600 is then deactivated 808 either automatically or manually when the user selects button 608.

During performance 802 of the heating cycle, controller 620 activates 810 heater 618 and pump 616. Heater 618 heats dryer cartridge 102 while pump 616 channels or directs air through dryer cartridge 102. The heat and the air flow remove liquid vapors and/or liquid particles from dryer cartridge 102, especially from capture portion 170 (shown in FIGS. 6 and 7). Controller 620 controls heater 618 to heat dryer cartridge 102 to a temperature within a predetermined range of temperatures and maintains the temperature of dryer cartridge 102 within the predetermined range of temperatures during the heating cycle. After the heating cycle, dryer cartridge 102 is allowed to cool to a predetermined temperature that is below the predetermined range of temperatures during the cooling cycle.

During the heating cycle, controller 620 monitors 812 a temperature of dryer cartridge 102 and/or chamber 612 and a pressure of air flow through and/or into dryer cartridge 102. For example, controller 620 periodically receives temperature and pressure measurements during the heating cycle to automatically control a temperature of heater 618 and an air flow of pump 616. More specifically, controller 620 receives a signal indicating temperature measurements from the temperature sensor and a signal indicating pressure measurements from the pressure sensor. Safety controller 622 also receives the signal indicating temperature measurements from the temperature sensor. Controller 620 controls heater 618 based on the temperature measurements to maintain the temperature within the predetermined range of temperatures. For example, controller 620 cycles heater 618 on and off during the heating cycle to maintain the temperature. More specifically, at an upper temperature of the range, controller 620 cycles heater 618 off, and at a lower temperature of the range, controller 620 cycles heater 618 on.

Controller 620 also compares the temperature and pressure measurements to thresholds to determine 814 if the measurements are within an appropriate range. More specifically, controller 620 compares the measured temperature to the maximum temperature threshold to determine 814 whether the temperature is within an appropriate range. When the measured temperature is less than the maximum temperature threshold, controller 620 continues performing 802 the heating cycle for a predetermined period of time then deactivates 816 heater 618 and pump 616. When the measured temperature is equal to or more than the maximum temperature threshold, controller 620 and/or safety controller 622 deactivates 818 heater 618 and pump 616, and notifies 806 the user that the drying cycle has been ended. In the exemplary embodiment, notification 806 includes indicating to the user a reason that the drying cycle was ended.

Further, controller 620 compares the measured pressure to a maximum pressure threshold and a minimum pressure threshold to determine 814 whether the pressure, and thus the air flow rate, is within an appropriate range. When the measured pressure is less than the maximum pressure threshold and above the minimum pressure threshold, controller 620 continues performing 802 the heating cycle for a predetermined period of time then deactivates 816 heater 618 and pump 616. When the measured pressure is equal to or more than the maximum pressure threshold or equal to or less than the minimum pressure threshold, controller 620 deactivates 818 heater 618 and pump 616, and notifies 806 the user that the drying cycle has been ended. In the exemplary embodiment, notification 806 includes indicating to the user a reason that the drying cycle was ended. While heating cycle is being preformed 802, controller 620 controls visual indicator 610 to be continuously lighted such that visual indicator 610 is solid during the heating cycle.

During the cooling cycle, controller 620 continues to monitor 820 the temperature of dryer cartridge 102. More specifically, controller 620 monitors 820 temperature measurements until the temperature of dryer cartridge 102 and/or chamber 612 is equal to or less than a predetermined temperature that is below the predetermined range of temperatures of the heating cycle. In a particular embodiment, the predetermined temperature is a temperature at which a user can safely handle dryer cartridge 102. As dryer cartridge 102 cools, controller 620 activates 822 visual indicator 610 to periodically be lighted such that visual indicator flashes or blinks during the cooling cycle. When dryer cartridge 102 is equal to or less than the predetermined temperature, controller 620 deactivates visual indicator 610 and/or lights another visual indicator, such as a green LED.

During the drying cycle, controller 620 can display a status of regenerator 600 and/or the drying cycle on display 606. More specifically, controller 620 can display any of the following information on display 606 and/or using visual indicator 610: a status such as "searching," "loading," and/or "calculating"; an error or fault notification; a specific error or fault that occurred; a notification that regenerator 600 is ready for dryer cartridge 102 to be inserted; a notification that dryer cartridge 102 is heating; a notification that dryer cartridge 102 is cooling; a notification that the drying cycle is complete; a current temperature during the heating cycle and/or the cooling cycle; a notification that the drying cycle has aborted for restricted air flow; a notification that the drying cycle has aborted because no dryer cartridge 102 is present within chamber 612; a notification indicting whether the temperature has reaches a target temperature by a predetermined time; and/or a notification that the drying cycle has aborted because the temperature is too high.

The embodiments described herein provide systems and methods for drying a removable dryer cartridge. More specifically, the herein-described dryer cartridge can be removed from a detector system and placed into a regenerator. The herein-described regenerator is configured to dry the dryer cartridge such that the dryer cartridge does not need to be replaced when the dryer cartridge has reached a predetermined liquid concentration. Because the dryer cartridge can be dried and re-used, a cost of maintaining and/or owning the herein-described detection system assembly is reduced as compared to systems in which a dryer cartridge is replaced rather than re-used. Further, because the detection system assembly described herein uses one dryer at a time, the detection system assembly can in a handheld, portable device.

A technical effect of the systems and methods described herein includes at least one of: (a) directing an air flow through the detector assembly to transport the substance through the detector assembly; (b) directing the air flow through the dryer cartridge to remove at least one of liquid particles and liquid vapors from the air flow; (c) identifying at least one of a chemical and a biological material of the substance using an output of the detector assembly; (d) determining whether the dryer cartridge has been wetted; and (e) removing the dryer cartridge from the detector system when the dryer cartridge is determined to be wetted.

Further, another technical effect of the systems and methods described herein includes at least one of: (a) performing a heating cycle during which the dryer cartridge is heated to a temperature within a predetermined range of temperatures; and (b) performing a cooling cycle during which the dryer cartridge is cooled to a predetermined temperature that is below the predetermined range of temperatures, the heating cycle and the cooling cycle defining a drying cycle.

Exemplary embodiments of a detection system assembly, a dryer cartridge, and a regenerator and methods for making and using the same are described above in detail. The methods and systems are not limited to the specific embodiments described herein, but rather, components of systems and/or steps of the methods may be utilized independently and separately from other components and/or steps described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:
1. A detection system assembly comprising:
a detector system including a housing comprising:
a sample port configured to receive a sample of an unknown substance;
a detector assembly in flow communication with the sample port; and
a pump in flow communication with the detector assembly; and
a dryer cartridge removably coupled to an outer surface of the housing of the detector system, the dryer cartridge in flow communication with the pump and the detector assembly.

2. A detection system assembly in accordance with claim 1, wherein the detector assembly comprises a desorber configured to heat the sample.

3. A detection system assembly in accordance with claim 1, wherein the detector assembly comprises at least one of an ion mobility spectrometer and an ion trap mobility spectrometer.

4. A detection system assembly in accordance with claim 1, wherein the dryer cartridge comprises a coupling portion configured to removably couple the dryer cartridge to the housing.

5. A detection system assembly in accordance with claim 1, wherein the dryer cartridge comprises:
an inlet configured to receive air flow from the pump;
an outlet configured to discharge air that is directed to the detector assembly; and
a capture portion positioned between the inlet and the outlet, the capture portion configured to capture at least one of liquid particles and liquid vapors from the air flow.

6. A detection system assembly in accordance with claim 5, wherein the dryer cartridge further comprises a coupling plate configured to couple to the capture portion of the dryer cartridge to the housing of the detector system to secure the dryer cartridge to the housing.

7. A detection system assembly in accordance with claim 1, wherein the detector system having the dryer cartridge coupled thereto forms a portable, handheld device weighing less than 10 pounds.

8. A dryer cartridge for use with a detector system, the dryer cartridge comprising:
an inlet configured to receive an air flow;
an outlet configured to discharge air;
a capture portion between the inlet and the outlet, the capture portion configured to capture at least one of liquid particles and liquid vapors from the air flow through the inlet; and
a coupling plate configured to removably couple the dryer cartridge to an outer surface of a housing of the detector system, the dryer cartridge configured to receive the air flow from a first component of the detector system and discharge the air into at least a second component of the detector system when the dryer cartridge is coupled to the detector system.

9. A dryer cartridge in accordance with claim 8, wherein the capture portion comprises sieve material and a housing, the housing coupled to the coupling plate such that the sieve material is enclosed by the housing and the coupling plate.

10. A dryer cartridge in accordance with claim 8 further comprising a gasket coupled between the capture portion and the coupling plate, the gasket configured to isolate a cavity of the capture portion from ambient conditions.

11. A dryer cartridge in accordance with claim 10, wherein the capture portion comprises a housing having a plurality of baffles adjacent a first side of the gasket.

12. A dryer cartridge in accordance with claim 10, wherein the coupling plate is positioned adjacent a second side of the gasket opposite the first side of the gasket.

13. A dryer cartridge in accordance with claim 8, wherein the coupling plate comprises at least one aperture defined therethrough, the at least one aperture configured to receive a fastener therethrough, the fastener configured to couple to the detector system.

14. A method for assembling a detection system assembly including a detector system and a dryer cartridge, the method comprising:
   providing the detector system including a housing;
   providing the dryer cartridge; and
   removably coupling the dryer cartridge to an outer surface of the housing of the detector system to form the detection system assembly.

15. A method in accordance with claim 14, wherein providing the dryer cartridge further comprises assembling the dryer cartridge by:
   providing a housing, sieve material, a gasket, and a coupling plate;
   positioning the sieve material within the housing;
   positioning the gasket adjacent the housing; and
   coupling the coupling plate to the housing to secure the gasket between the coupling plate and the housing.

16. A method in accordance with claim 14, wherein removably coupling the dryer cartridge to the housing of the detector system further comprises:
   inserting a fastener at least partially through the dryer cartridge; and
   securing the fastener to the outer surface of the detector system housing.

17. A method for operating a detection system assembly that includes a detector system and a dryer cartridge removably coupled to the detector system, the method comprising:
   inserting a sample of a substance into a detector assembly of the detection system assembly;
   directing an air flow through the detector assembly to transport the substance through the detector assembly;
   directing the air flow through the dryer cartridge to remove at least one of liquid particles and liquid vapors from the air flow; and
   identifying at least one of a chemical and a biological material of the substance using an output of the detector assembly.

18. A method in accordance with claim 17, further comprising:
   determining whether the dryer cartridge has been wetted; and
   removing the dryer cartridge from a housing of the detector system when the dryer cartridge is determined to be wetted.

19. A method in accordance with claim 18, wherein determining whether the dryer cartridge has been wetted further comprises determining that the dryer cartridge has been wetted when the dryer cartridge has a concentration of liquid that is more than a liquid concentration threshold.

20. A method in accordance with claim 18, wherein determining whether the dryer cartridge has been wetted further comprises determining that the dryer cartridge has been wetted when at the dryer cartridge has been used to perform a predetermined number of analyses.

21. A method in accordance with claim 18, wherein determining whether the dryer cartridge has been wetted further comprises determining that the dryer cartridge has been wetted when at the dryer cartridge has been used for a predetermined length of time.

* * * * *